(12) United States Patent
Pfeiffer

(10) Patent No.: US 7,582,855 B2
(45) Date of Patent: Sep. 1, 2009

(54) HIGH-SPEED MEASURING DEVICE AND METHOD BASED ON A CONFOCAL MICROSCOPY PRINCIPLE

(75) Inventor: Joachim Pfeiffer, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 23 days.

(21) Appl. No.: 10/593,471

(22) PCT Filed: Mar. 18, 2005

(86) PCT No.: PCT/EP2005/051276

§ 371 (c)(1), (2), (4) Date: Sep. 19, 2006

(87) PCT Pub. No.: WO2005/091046

PCT Pub. Date: Sep. 29, 2005

(65) Prior Publication Data

US 2007/0194214 A1    Aug. 23, 2007

(30) Foreign Application Priority Data

Mar. 19, 2004 (DE) ............... 10 2004 014 048

(51) Int. Cl.
*G02B 7/04* (2006.01)
*G01B 11/24* (2006.01)
*G02B 21/00* (2006.01)

(52) U.S. Cl. ................ 250/201.3; 356/601; 359/368
(58) Field of Classification Search ............ 250/201.3; 359/368; 356/601–609
See application file for complete search history.

(56) References Cited

U.S. PATENT DOCUMENTS 6,300,618 B1    10/2001    Tanaami et al.

(Continued)

FOREIGN PATENT DOCUMENTS

| DE | 10051505 | 5/2002 |
|---|---|---|
| EP | 1186928 | 3/2002 |
| GB | 2077421 | 12/1981 |

OTHER PUBLICATIONS

English Abstract of DE 10051505.

*Primary Examiner*—Thanh X Luu
(74) *Attorney, Agent, or Firm*—Dykema Gossett PLLC

(57) ABSTRACT

The invention relates to a measuring device and a method based on a confocal microscopy principle. The inventive device comprises a light source (1), a diaphragm unit (3) for limiting a beam, an imagine optical system (4) for focusing the light (5) which is irradiated by said source on a measurable object (6) and passes through said diaphragm unit. Said device also comprises an optical system (10) for receiving the light (5) reflected from the object and passing through said optical system or another diaphragm unit disposed in an observation beam (7) and an image receiver (10) which is provided with at least two radiation-sensitive sensor elements (13, 14) (pixel). Said invention is characterized in that, in order to obtain the image of an altitude information-containing measurement, the device is also provided with means (11) for modifying the beam optical path length disposed between the light source (1) and/or the image receiver (10), on one side, and the object (6) on the other and the optical distance (d) of a focal point is modifiable in a predetermined manner. In addition, said intention makes it possible to influence the dependence of an accumulation of charges (Q13, Q14) in at least two sensor elements (13, 14) on the light intensity of the observation beam (7) during the exposure time in such a way that a correlation associated with the optical distance (d) of an image plane can be carried out by the imagine optical system (4), thereby making it possible to reconstitute the altitude co-ordinate (zs) of the object by distributing the intensity values obtained during the exposure time from at least two sensor elements (13, 14).

14 Claims, 11 Drawing Sheets

U.S. PATENT DOCUMENTS 6,697,163 B2 * 2/2004 Fukuda et al. .............. 356/609
2002/0027594 A1 3/2002 Beier et al.
2004/0051879 A1 3/2004 Schick

* cited by examiner

HIGH-SPEED MEASURING DEVICE AND METHOD BASED ON A CONFOCAL MICROSCOPY PRINCIPLE

BACKGROUND OF THE INVENTION

1. Field of the Invention

The invention relates to a scanning system and method based on the principle of confocal microscopy.

2. The Prior Art

Such scanning systems are used for scanning an object and for enabling both scanning of a point along an axis (two-dimensional scanning) and scanning of a surface disposed about an axis (three-dimensional scanning). Thus, such a device is suitable for a point sensor and a flat panel sensor.

The basic principles of confocal 3D scanning are known. The determination of the altitude of a point on an object is achieved in the prior art by determining, for each point of a drilled board constituting an aperture array, that position of the object, relative to the imaging optics or the entire scanning device, at which the greatest amount of light travels back through the drilled board. In addition, during the movement of the object relative to the imaging optics, a plurality of image frames is recorded and for each dot in the image that frame in the frame sequence is determined in which the intensity is greatest. The vertical profile of the object can be determined from the knowledge of the position of the image frame within the frame sequence. However, typically frame sequences of some 10 to 100 frames must be recorded, so that the measuring procedure, using current recording technologies, takes several seconds or even longer. To shorten the total measurement time to one acceptable for intraoral dental imaging, considered to be approximately 200 ms, it is necessary to use extremely complex video technology and data evaluation, or to lose accuracy in at least one of the three dimensions. Moreover, high demands are made on the mechanics for producing the relative motion between the object and the imaging optics.

In the prior art, it is known that a rapid change in the distance between an object and the imaging optics can be achieved by inserting an element made of a medium which has a different optical density and a variable thickness, and is moved in such a way that the effective thickness is varied over time. A suitable medium for this purpose is glass, for example.

Furthermore, 3D scanning techniques used in an intraoral camera for scanning teeth are also known, which work on the principle of phase shift triangulation.

Moreover, the use of point sensors or line sensors is well known in current 3D scanning procedures, the 3D-object being moved relatively to the sensor during the measuring operation, which is often referred to as scanning.

SUMMARY AND OBJECTS OF THE INVENTION

According to the invention the scanning system based on the principal of confocal microscopy comprises a light source, imaging optics for focusing the light emitted from the light source onto the object to be measured, and an image detector to receive the light of a point on the object that is backscattered from the object, passing through the same imaging optics to at least two radiation-sensitive sensor elements. The characterizing feature of the scanning device is that at least two sensor elements are assigned to a point on the object illuminated by the imaging optics. The scanning device contains means for varying the length of the optical path, these being located in the optical path between the aperture array and the object, the optical distance of the image plane from the imaging optics being varied in a prescribed way. The relationship between the accumulation of charges in the at least two sensor elements and the light intensity of the observation beam path during the exposure period can be influenced in such a way that a relationship with the optical distance of the image plane from the imaging optics can be created so that an altitude coordinate of the object can be reconstructed from the distribution of the intensity values acquired from the at least two sensor elements during an exposure period. Advantageously the imaging area of the object in the plane of the radiation-sensitive sensor elements is at least large enough for at least one of the two sensor elements to lie completely within the imaging area during an exposure period.

Reconstruction is possible by assigning information acquired from the two sensor elements to each change in length of the optical path. Using a device based on this principle, it is possible to carry out the measurement in a comparatively short period of time by using the method of confocal microscopy. This requires only one exposure, during which an adjustment of the optical distance takes place.

In addition, the scanning device can comprise an aperture array for generating a brightness distribution on the object. This makes it possible to examine more than one point on the object at a time.

An advantageous embodiment of the scanning device is characterized in that several points on the object can be detected using the aperture array, wherein there should be at least as many interacting groups of sensor elements as there are points that are to be detected on the object. The delimitation of the altitude coordinates is improved in this way.

Furthermore, in the observation beam path, the scanning device can comprise means between the object and the detector for deflecting the observation beam path. Thus the light and the receiver optics can be spatially separated from each other, which facilitates the configuration of the required components in narrow spaces.

This deflection means is advantageously in the form of a beam splitter.

This deflection means is preferably disposed between the aperture array and the light source. In addition, it can be disposed between the imaging optics and the aperture array.

In an advantageous embodiment of the scanning device, a moving aperture is provided, which shades the sensor elements at least partially as a function of the degree of movement.

The aperture could be designed in such a way that a movement of the aperture causes a reduction in the shading of the at least one sensor element and simultaneously an increase in the shading of the at least one other sensor element.

Furthermore, in a starting position, the aperture can shade one part of the sensor elements completely and, in an end position, shade the other part of the sensor elements completely and, in an intermediate position, shade both a portion of one sensor element and a portion of the other sensor element. This can be effected using the same opaque component of the aperture. The largest possible differences in the intensity of the sensor elements can thus be achieved and the signal-to-noise ratio can thus be increased.

The degree of the shading of the one part of the sensor elements is advantageously equal to the degree of non-shading of the other part of the sensor elements. In this way, a linearization of the relationship acquired from the distribution of the intensity values of the at least two sensor elements is made possible, and calibration of the system is simplified.

In an advantageous development of the invention, the aperture array is designed for two-dimensional scanning of the object. The aperture array is in the form of a two-dimensional structure for this purpose and comprises a plurality of individual, spaced apertures. The distance between the individual apertures sets a pulse duty ratio of the aperture array. Such aperture arrays are well known in confocal measurement technology.

Advantageously, adjusting means are provided in order to adjust the aperture array so as to detect, in a second scan, regions which were not imaged in a first scan. This leads to an increase in the resolution beyond the extent set by the pulse duty ratio.

A line sensor is suitable as an image detector for creating two-dimensional imaging, wherein the one dimension is particularly an altitude coordinate. A flat panel sensor is suitable as an image detector for three-dimensional imaging with an altitude coordinate.

The image detector is advantageously in the form of a CCD sensor. Alternatively, the image detector may be in the form of a CMOS sensor.

The sensitivity of the sensor elements can be altered with the aid of a beam splitter disposed in the observation beam path, which beam splitter transmits the same image to a second sensor element, cross-fading between the two sensor elements being effected during the scanning period by means of electronic and/or optical auxiliary means. This allows for the operation of two independent sensors.

Advantageously, the sensitivity of one of the at least two interacting sensor elements increases and that of the other decreases as the length of the optical path progressively changes. It is thus possible to create a simple correlation between the information provided by the sensor elements and the altitude to be determined.

It is expedient to adapt the average scanning distance of the aperture array to the desired measuring accuracy.

The process of the invention consists in emitting light from a light source onto an object to be measured according to the basic principle of confocal microscopy, wherein the light is focused using imaging optics and in which additionally the light of a point on the object is backscattered from the object and passes through the same imaging optics to be detected by means of an image detector having at least two radiation-sensitive sensor elements. The scanning is characterized in that at least two sensor elements are assigned to an illuminated point on the object. Furthermore, the optical distance of the image plane is variable in a predetermined manner using means disposed in the optical path between the aperture array and the object and the relationship between the accumulation of charges created in the at least two sensor elements and the light intensity in the observation beam path is changed during an exposure period using means in such a way that a correlation between the accumulation and the optical distance of the image plane from the imaging optics is created so that an altitude coordinate of the object can be reconstructed from the distribution of the intensity values acquired from the at least two sensor elements during an exposure period. The imaging area of the object in the plane of the radiation-sensitive sensor elements is at least large enough to ensure that at least one of the two sensor elements lies completely within the imaging area during an exposure period.

BRIEF DESCRIPTION OF THE DRAWINGS

The process of the invention is explained below with reference to the drawings, in which.

DETAILED DESCRIPTION OF EXEMPLARY EMBODIMENTS OF THE INVENTION

Figure 1:
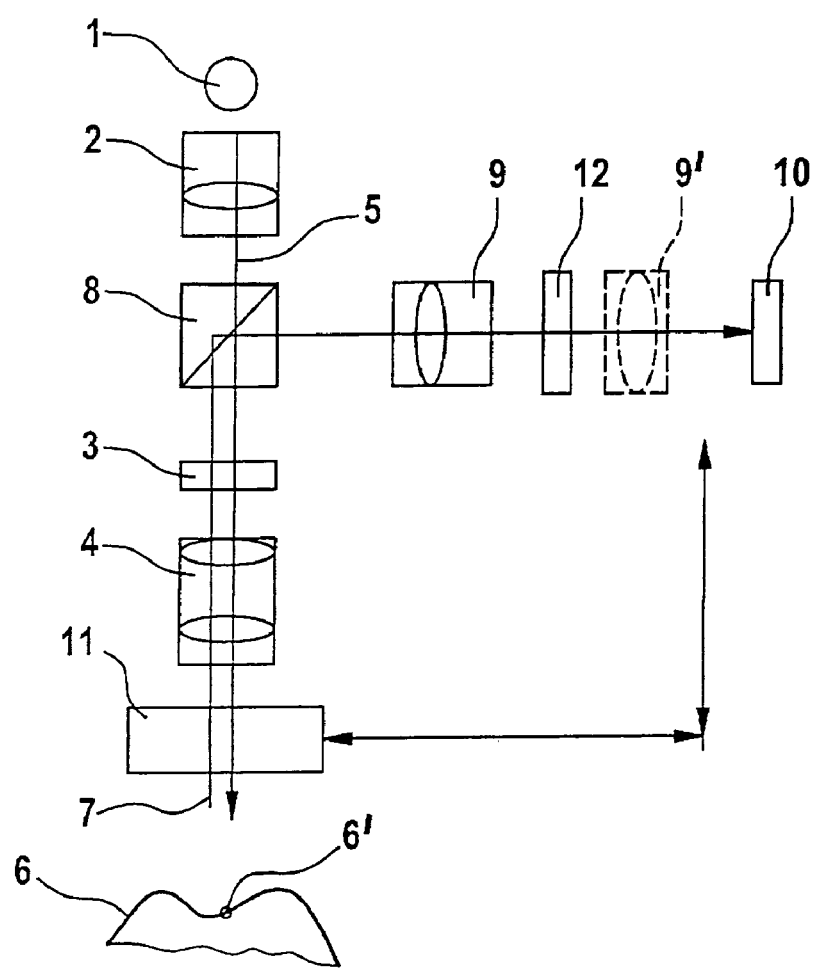
FIG. 1 shows a basic structure of the scanning device according to the basic principle of confocal microscopy in an embodiment according to the invention.

FIG. 1 shows a basic structure of the scanning device according to the basic principle of confocal microscopy. The scanning device comprises a light source 1, which typically emits monochromatic or white light.

The light source 1 is reproduced in a suitable way on an aperture array 3 using optics 2. The aperture array 3 can be in the form of a drilled board. In the case of more developed applications, an arrangement of micro-lenses can be used, if desired. This arrangement can be moved rapidly, if appropriate, for the full-area scanning of the object, in which case an image must be created in each position.

By means of imaging optics 4, which are usually designed telecentrically, the light emitted from the aperture array 3 is reproduced on an object 6 to be scanned. The optical distance of the imaging optics 4 relative to the object 6 can be changed so that different altitude lines of the object to be scanned are located in the image plane of the imaging optics. The light spots created on this path on the object 6 to be scanned are backscattered from the latter and pass through the aperture array 3 as the observation beam path 7 in a direction opposite to that of light 5.

The quantity of backscattered light always achieves a maximum for the object points 6' of the object 6, which currently lie in the image plane of the imaging optics 4. In this case the light intensity is clearly stronger than that of the light backscattered from outside the image plane.

The light of the observation beam path 7 penetrating the aperture array 3 from behind is reproduced by means of a beam splitter 8 and receiver optics 9 on an image detector 10, by means of which an electronic signal is obtained, which is fed to a computer for evaluation.

The change of the optical distance between the imaging optics 4 and the object 6 takes place using means 11 for changing the length of the optical path.

This element can be inserted between the imaging optics and the object or between the aperture array and said optics.

It is neither necessary for a linear correlation to exist between the movement of this element and the sharp region in the space accommodating the object, nor is it necessary for a definite altitude line in the object to be sharply reproduced at the same time, since such behavior can be corrected by appropriate methods of calibration.

A preferred arrangement of such an element as a means 11 for changing the length of the optical path in the optical path between the aperture array 3 on the one hand and the object 6 on the other can comprise two glass wedges which can be moved relatively to one another so that the result is a glass plate of variable thickness, see FIG. 12.

The effective length of the optical path can also be changed using a folded beam path and a moveable reflector. The drive of the reflector can be designed advantageously using a moving coil similar to that used in a loudspeaker, see FIG. 13.

A moveable aperture 12 is provided between the aperture array 3 and the image detector 10 in the observation beam path 7, which aperture 12 is located as close as possible in front of the image detector 10 in this embodiment. It is essential that this aperture 12 be arranged in a plane in which the aperture array 3 or the surface of the image detector 10 is reproduced with sufficient sharpness.

Thus the beam path downstream of the aperture array could be formed so as to give rise to another image plane for the aperture array in addition to the one already present, in which the image detector 10 is located. In this case the aperture could be disposed in this image plane. The design and mode of operation of this aperture is explained below.

An alternative arrangement of the imaging optics in the observation beam path is made possible by omitting the imaging optics 9 and adding the imaging optics 9' between the moveable aperture 12 and the image detector 10.

Figure 2:
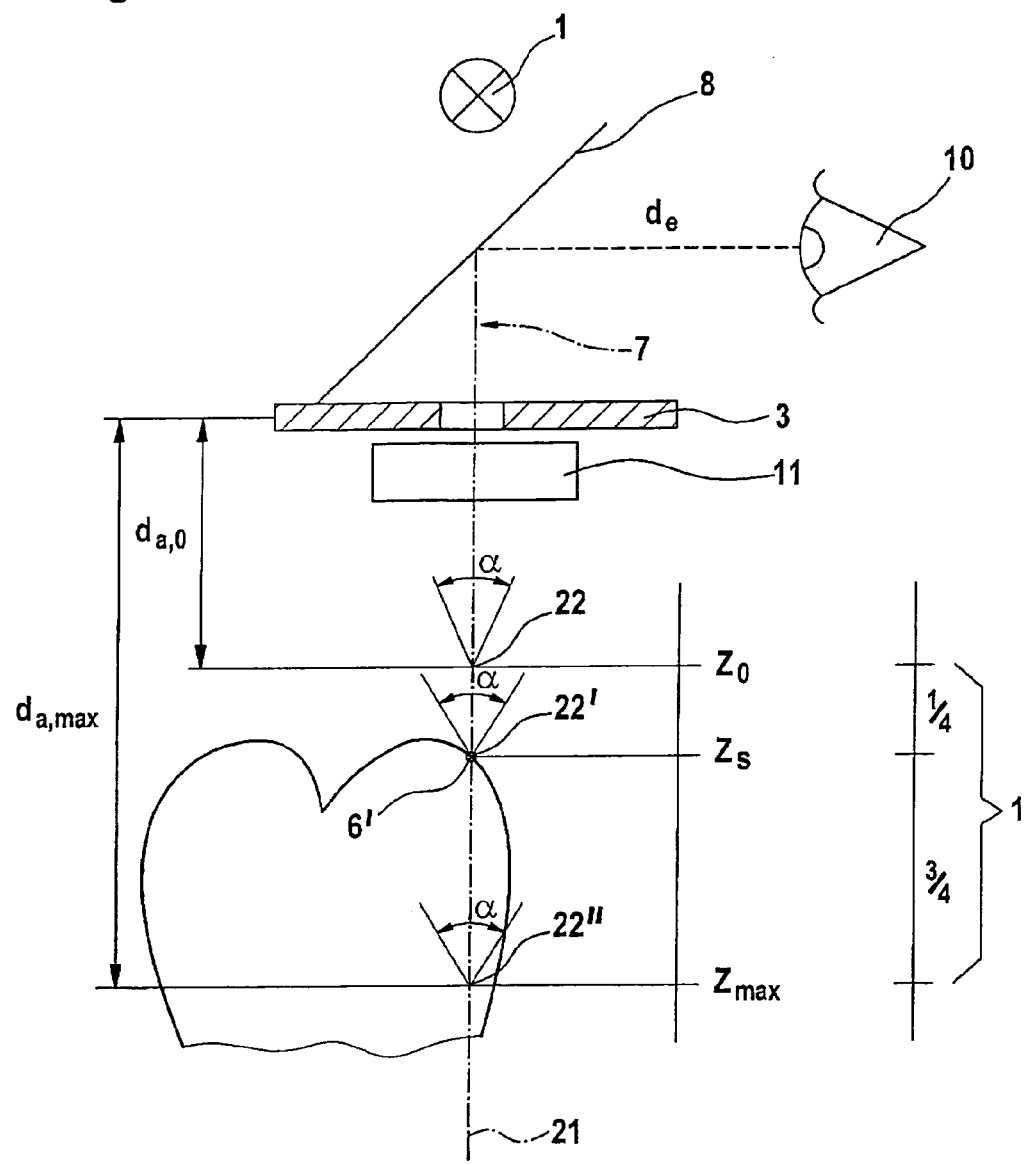
FIG. 2 shows the basic scanning problem, illustrated with reference to a tooth, FIG. 3 clarifies the scanning problem with reference to a cavity.

FIG. 2 illustrates the basic scanning problem with reference to the scanning of a point on the object 6' along an axis 21, on which the observation beam path 7 is also located up to the site of deflection at the beam splitter 8. The object to be scanned 6, in this case a tooth, comprises a three-dimensional surface contour, which is to be reproduced as a 3D model. In a two-dimensional image, as in the case of a conventional video image, information about the shape on the x and y coordinates is obtained. However, the altitude levels along the z coordinate remain unknown. When scanning, the light emitted by the light source 1 is focused in such a way that light that has passed through the aperture array 3 produces a focal point 22 of an aperture at the altitude $z_0$ at the commencement of the scan. A distance $d_a$, o then exists between the aperture array 3 and the focal point 22.

The light spot has an aperture angle $\alpha/2$ of from 1° to 15°.

By altering the length of the optical path between the imaging optics 4 and the object 6 using means 11, the focal point 22 is displaced until it reaches the surface of the object 6 in the point of the object 6 at altitude $z_s$, which corresponds to approximately one quarter of the measuring range in this case.

In this position, the point 6' on the object coincides with the focal point 22'. It is just in this position that the light being emitted from the aperture is most concentrated on a point of the object surface and the light backscattered from the object point 6' is optimally reproduced by the aperture hole so that the image detector discerns an intensity peak for the associated point exactly in this position. This corresponds to the basic principle of confocal microscopy.

At a distance $d_{a,max}$ the image of the aperture on the object 6 is in turn blurred and therefore very little light reaches the image detector.

During the measurement, scanning in the z direction is effected by changing the length of the optical path, which can take place by a mechanical displacement of the imaging optics or by changing the optical density in the beam path or by other means known in the prior art. This alteration of the length of the optical path takes place during a single exposure period.

Figure 3:
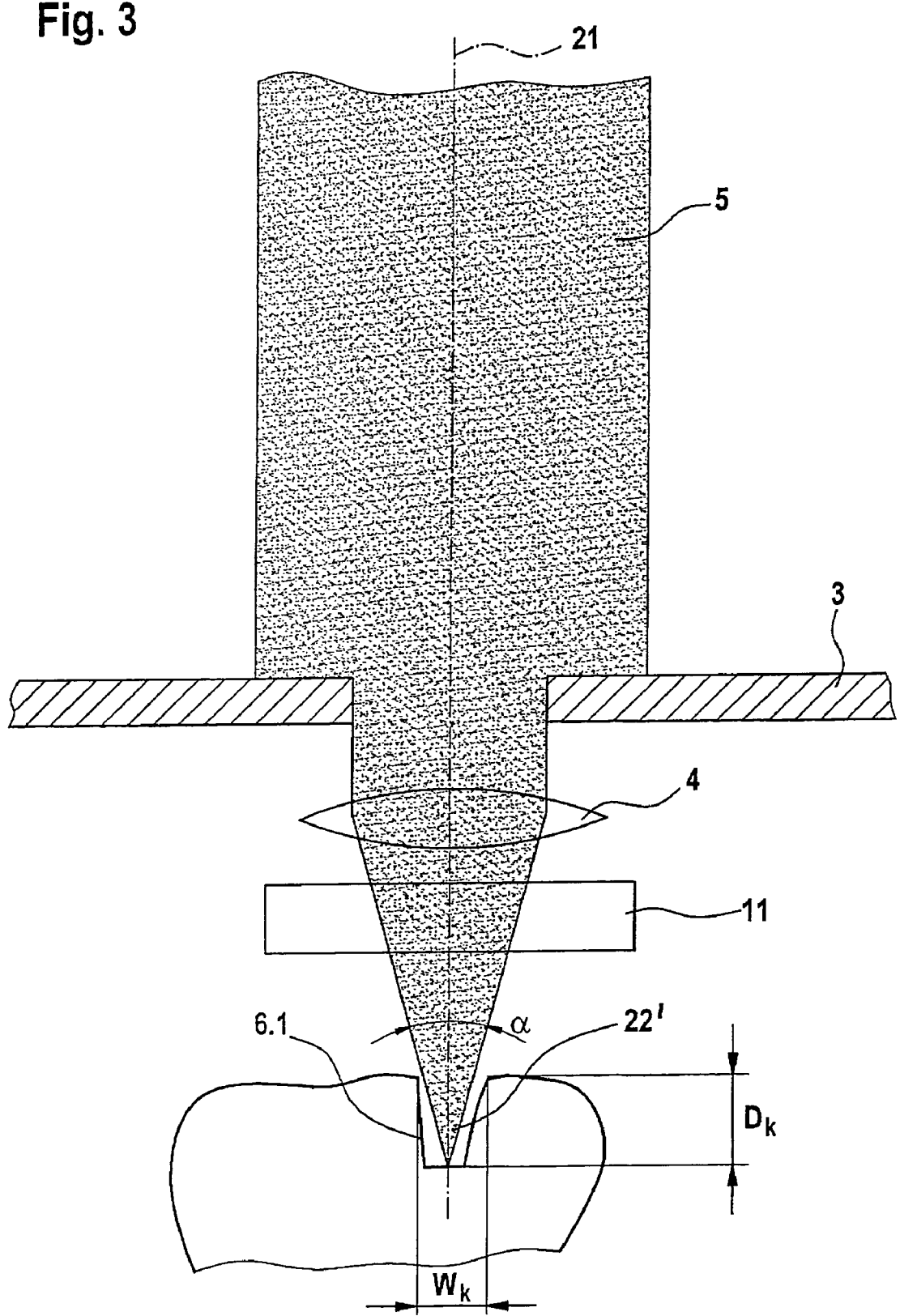

FIG. 3 clarifies the basic scanning problem with reference to a cavity 6.1 present on the tooth surface 6. The angle $\alpha$ present due to the aperture angle of the aperture 3 and the focal length of the imaging optics 4 must not be too wide, in order to achieve the best possible resolution of the surface structure. In order for a surface point 6' located in a cavity having a width $W_K$ and a depth $D_K$ from the focal point 22' to be illuminated with full intensity, it is necessary for the aperture angle to be smaller than the maximum angle given by the geometric ratio of width to depth of the cavity.

Figure 4A:
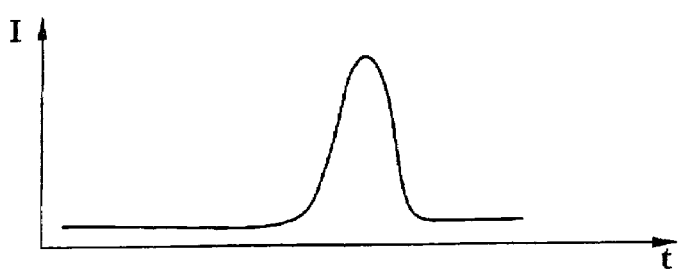
FIG. 4A shows the time/intensity curve of the light that is backscattered from a point of the object behind the aperture array in the observation beam path, during the change of d (the temporal position of the intensity maximum contains information on the altitude z of the point on the object)

In FIG. 4A, an intensity distribution in the observation beam path 7 between the aperture array 3 and the image detector 10 as shown in FIG. 2 is illustrated. In the region in which the light is focused on the surface of the object to be examined, an intensity peak results during the exposure period at altitude $z_s$, in this case after approximately one quarter of the change of the optical distance has been carried out. Said intensity peak takes the form of a clearly visible point. It is obvious that the optical distance need not correspond linearly to the actual 3D image. The ultimate aim here is to provide altitude coordinates of the object to be scanned. All the same, it is still an advantage if linearization of the correlation between the position of the aperture array and that of the focal point can be effected.

Figure 4B:
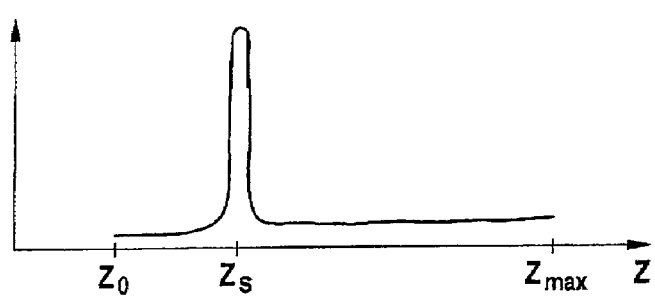
FIG. 4B shows an intensity distribution of the change in the optical path occurring during a scan of the object.

In FIG. 4B the intensity curve of the light of the observation beam path 7 in the aperture array 3 is shown, which light is backscattered from the object 6. The vertical axis corresponds to the intensity of the light, and the horizontal axis corresponds to the time t during the exposure period T of the image detector 10. The image detector 10 is exposed during the entire exposure period T, wherein the clearly visible intensity increase occurs exactly when the assigned object point 6' lies in the sharp area of the image created by the imaging optics. By contrast, the intensity values outside this sharp area are clearly lower since the light spot at object point 6' is larger.

Figure 5:
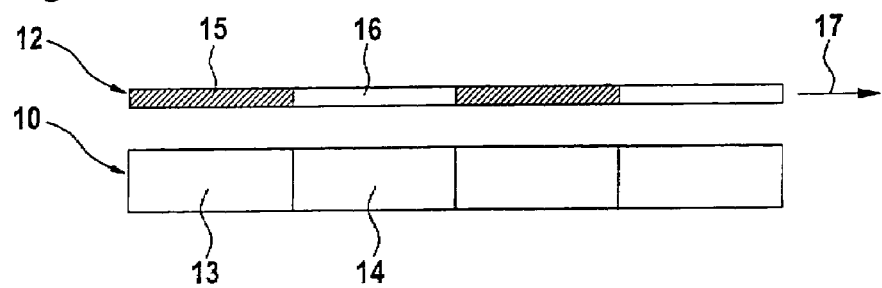
FIG. 5 is a lateral view of an aperture according to the invention, which is disposed close to the image detector comprising two interspersed matrices of sensor elements.

In FIG. 5, an exemplary embodiment of an aperture 12 is shown, which is located immediately adjacent to an image detector 10. The image detector 10 comprises a plurality of radiation-sensitive sensor elements 13, 14, which interact according to the invention. The aperture 12 is in the form of a light/dark pattern and thus has an opaque area 15 and a translucent area 16. Furthermore, the aperture 12 can move in the direction of the arrow 17 across the image detector 10 and the sensor elements 13, 14.

Examples of suitable hole patterns for the aperture 12 are striped patterns. However a checkerboard pattern is also suitable, as explained with reference to FIGS. 11A to 11C in detail. In the exemplary embodiment, the striped pattern corresponds to the size of the sensor elements 13, 14; ie one stripe of a striped pattern has the same width as the sensor elements 13, 14.

In the initial position illustrated, the sensor element 13 is completely shaded by the opaque area 15, while the second sensor element 14 is unshaded. Light directed towards the sensor elements 13, 14 therefore generates an informative electronic signal exclusively in the sensor element 14.

Figure 6:
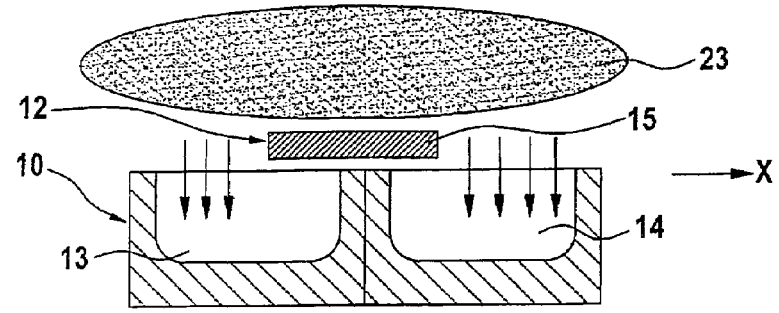
FIG. 6 is a schematic diagram of the image detector comprising two sensor elements.

In FIG. 6, a schematic diagram of the image detector 10 having the sensor elements 13, 14 is shown, wherein for the purpose of simplification, only the opaque area 15 of the aperture 12 is shown. The light spot 23 falls on the adjoining sensor elements 13, 14 as an image of the aperture array disposed in the observation beam path. The diameter of the light spot 23 is predetermined by the aperture array and dimensioned in such a way that both the sensor elements 13, 14 are completely covered. Furthermore, it is assumed that the intensity of the light in the light spot 23 is constant over the entire surface. The intensity itself is definitely variable with time. That is, the intensity can, of course, vary over a defined exposure period T, during which a change in the optical path also takes place. If the intensity does not change, the measuring point is beyond the measuring range.

It can be clearly seen that the opaque area 15 of the aperture 12 in the position illustrated shades both sensor element 13 and sensor 14 only partially so that only a fraction of the intensity of the light spot 23 is available to the sensor elements 13, 14 for generating the signal.

The portion of the light supplied to the respective sensor element 13, 14 can be changed by shifting the position of aperture 12.

Starting from the intensity curve shown in FIG. 4A, the intensity of the light incident on the sensor elements at different positions of the aperture 12 and the charges thus generated are explained with reference to FIGS. 7A to 7C assuming that all the unwanted signals such as dark current, noise and the portions of the intensity from planes that are not sharp are negligible and can be corrected by computerization.

Since the photons are converted to electric charges in the case of an electronic image detector, a curve of the intensity is shown here in a space axis of the sensor elements, here in the x-direction, at different times t or altitude coordinates z caused by a change in the length of the optical path. The aperture is also moved in this direction during the exposure period T. This movement is depicted as the translucent area 15 by broken lines. The accumulated intensity I and the electric charge Q caused thereby are drawn over the direction of movement of the aperture.

Figure 7A:
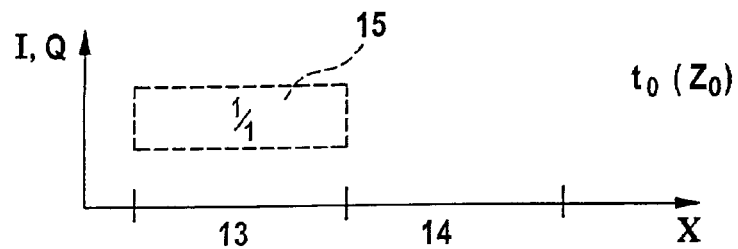
FIGS. 7A to 7C show the qualitative course of the intensity occurring in the sensor elements and the charges thus created.

The start of an exposure period T at the time $t_o$ is shown in FIG. 7A. The opaque area 15 of the aperture 12 shades the sensor element 13 over its entire extent in the x direction, whilst the sensor element 14 is without any shading over its entire length in the x-direction. However, since neither the dark current portion, nor the noise portion nor portions of blurred planes are taken into consideration, charges accumulated neither in the sensor element 13 nor in the sensor element 14 in this initial phase.

Figure 7B:
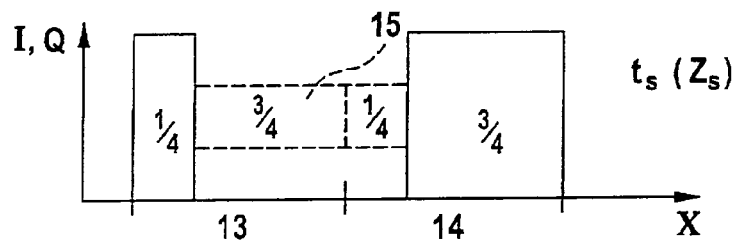
Figure 7C:
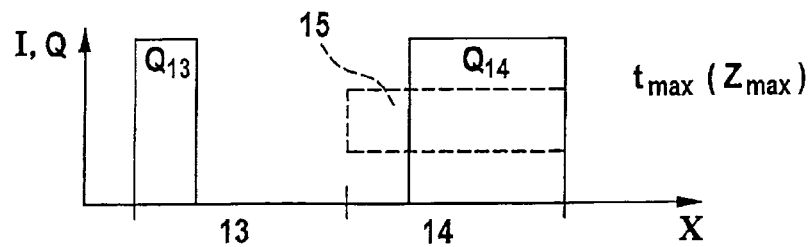

FIG. 7B shows the situation at the moment $t_s$ of incidence of the focal point on the surface of the object to be scanned having an altitude coordinate $z_s$. The optical path is adjusted in such a way that the focal point 22' of FIG. 2 lies on the surface of the object 6 to be examined, shown in FIG. 2. This causes the abrupt increase in the intensity shown in FIG. 4. However, since the opaque area 15 of the likewise adjusted aperture covers different parts of the two sensor elements 13, 14, different charges are accumulated in the two sensor elements 13, 14. These are illustrated for better understanding as ratios ¼ and ¾, which correspond to the inverse ratios of the shading of ¾ and ¼. Since no further exposure takes place during the additional exposure period up to the end of the exposure period T at time $t_{max}$, the charges $Q_{13}$, $Q_{14}$ accumulated due to the exposure according to FIG. 7B remain, in FIG. 7C, in the sensor elements 13, 14. The exact time of the exposure of the sharp layer can be determined from the difference and/or the ratio of the charges $Q_{13}$, $Q_{14}$. From the determination of this time, an altitude coordinate $z_s$ can be reconstructed from the knowledge of the changes in the optical path length on the one hand and the movement of the aperture 12 on the other hand. Said altitude coordinate reproduces a point on the surface of the object to be examined.

Even if no ideal ratios are present, the high intensity of the light spot results in a sufficiently large signal-to-noise ratio to make it possible to effect evaluation when the plane in which the focal point 22 lies reaches the surface of the object being examined.

The general approach is that the change in the length of the optical path in the beam path and the change in the sensitivity and/or in the unshaded area are synchronized, this implying, in the simplest case, that an aperture is moved from the described initial position to the described end position during the time in which the altitude region of interest is scanned by changing the length of the optical path. In the simplest case this is exactly the same period as the exposure time T for creating an image on the image detector.

Especially when use is made of CCD sensors or CMOS sensors, photons occurring during the entire exposure period are converted into an electric charge. A single exposure period is sufficient for a complete scan, which exposure period does not exceed a duration of 500 ms and preferably does not exceed 200 ms, while 50 ms is a typical value. In this period of time, it is still possible to create an image either freehanded or with the camera supported as required in the case of an intraoral camera.

Due to the special requirements involved, an altitude measuring range of from 12 mm to 20 mm can be required for intraoral cameras without the exposure period being too long and without jeopardizing accuracy.

In FIGS. 6 and 7A to 7C, a pair of sensor elements 13, 14 is observed on which light from an opening in the aperture array is reproduced. Taking into consideration the time/intensity profile behind the aperture array, for example behind the drilled board, the two sensor elements 13, 14 are almost non-illuminated except for a short period of time in which the assigned point of the object to be scanned lies in the sharp area. This quantity of light falls more on the first or more on the second sensor element 13, 14 of the image detector 10 depending on the position of the aperture and particularly of the opaque area 15. From the intensity acting on the sensor elements 13, 14, the time can thus be calculated at which the assigned object point was reproduced sharply. An altitude value is then assigned to the time using calibration data acquired by calibrating the scanning device. Thus the altitude of the object scanned can be calculated from the intensities in the two sensor elements 13, 14 forming an image on the image detector, which is to be read out.

As an alternative to a mechanically displaced aperture, it is possible to use appropriately controlled electrical means, eg an LCD element, or other optical components which permit a change in translucence, eg a combination of appropriately designed polarization filters having opaque and translucent regions.

Furthermore, it is neither strictly necessary for the translucent and opaque areas 15 of the aperture 12 to be exactly the same size, nor must these areas be exactly the same size as a sensor element. Complete covering of a sensor element is likewise hardly necessary since it is only important to achieve an unambiguous value distribution between the two sensor elements 13, 14.

Theoretically, it is possible to bundle a plurality of sensor elements in groups instead of using individual sensor elements and to take into account the behavior of groups of sensor elements instead of the behavior of individual sensor elements relative to one another.

Figure 8:
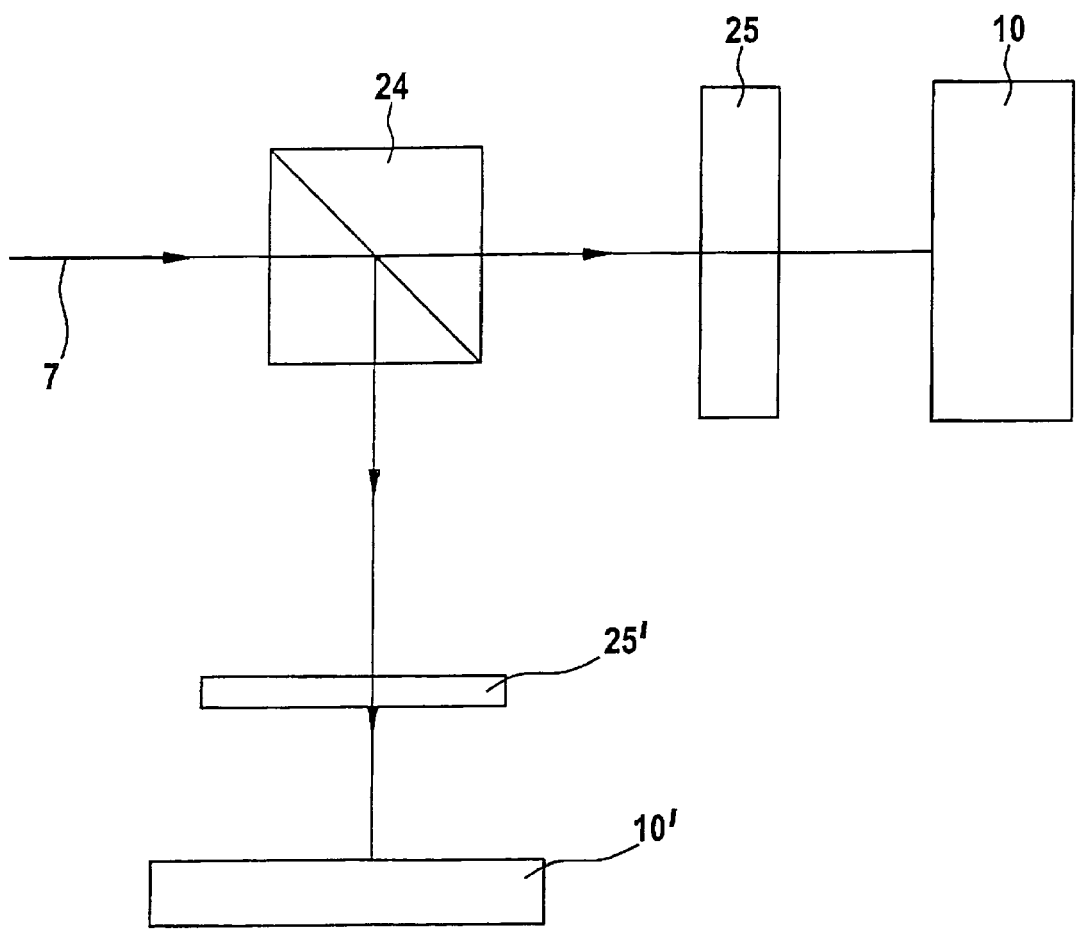
FIG. 8 shows an embodiment in which the same image is reproduced by means of a beam splitter on two spatially separated image detectors.

In FIG. 8, an embodiment is shown in which the same image is reproduced on two separate image detectors 10, 10' by means of a beam splitter 24. The temporally variable sensitivity of the spaced image detectors 10, 10' required according to the invention can be effected by shading by means of electronic or optical auxiliary means. LCD elements 25 and 25' are provided here by way of example, the translucence of which can be changed electrically. A computer can control this change, if appropriate. The control of the LCD elements 25 und 25' allows for a simultaneous increase of the shading of the one sensor element and a reduction of the shading of the other sensor element.

Figure 9A:
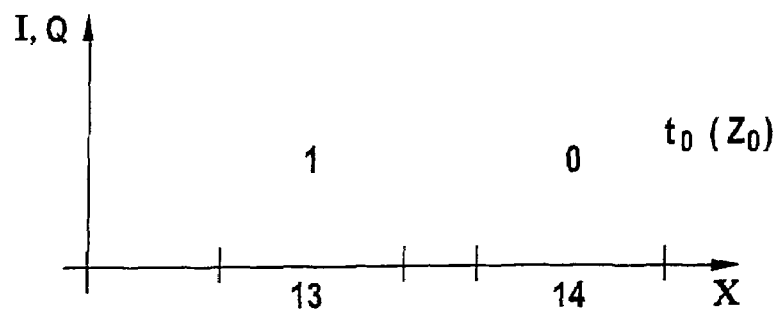
FIGS. 9A to 9C show the qualitative course of the intensity occurring in the sensor elements and the charges thus created in an embodiment according to FIG. 8, FIGS. 10A to 10C show different possible embodiments of image detectors that can be used according to the invention.
Figure 9B:
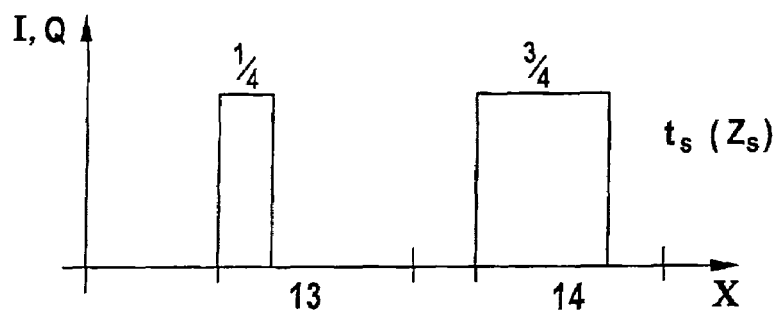
Figure 9C:
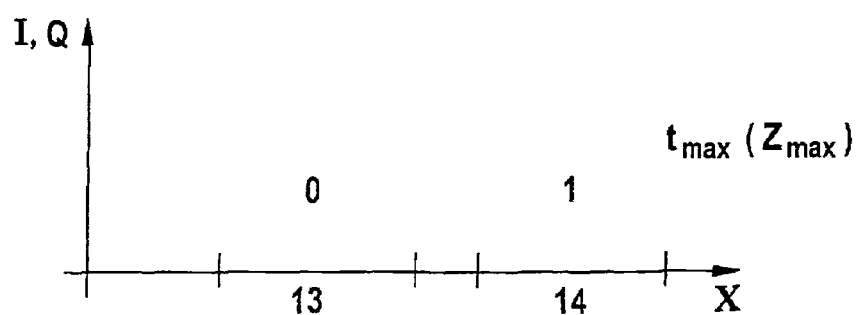

In FIGS. 9A to 9C, the illumination intensities of both sensors 10 and 10' used in FIG. 8 are shown with sensor elements 13, 14 that are present on separate sensors.

FIG. 9A shows a totally translucent aperture in front of the sensor element 13 and a totally opaque aperture in front of the sensor element 14 at a time $t_0$. Since, as illustrated in FIG. 2, the focal point 22 does not coincide with the surface point 6' on the object 6 at the time $t_0$, only very low light intensity will fall on the sensor element 13 and only a very low charge is accumulated, which is of no significance for the evaluation, as already explained with reference to FIG. 7A.

FIG. 9B shows the time $t_s$ at which the focal point coincides with the object point. At this point the apertures shadow the one sensor element to a definite degree and the other sensor element to a complementary degree, illustrated here as ratio ¼:¼ for clarification. Since the largest quantity of light is reflected at this time, the light intensity on the sensor elements 13, 14 is at its greatest.

FIG. 9C shows the intensity ratio at a later time $t_{max}$ at which, as opposed to FIG. 9A, the sensor element 13 is fully shaded and the full light intensity is fed to the sensor element 14. However, this light intensity, as is the case on sensor element 13 of FIG. 9A, is much less than at time $t_s$.

Figure 10A:
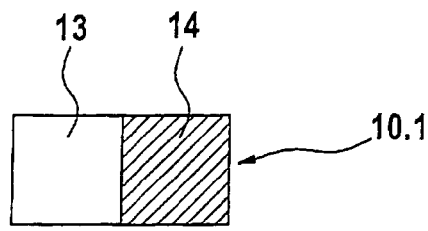
Figure 10B:
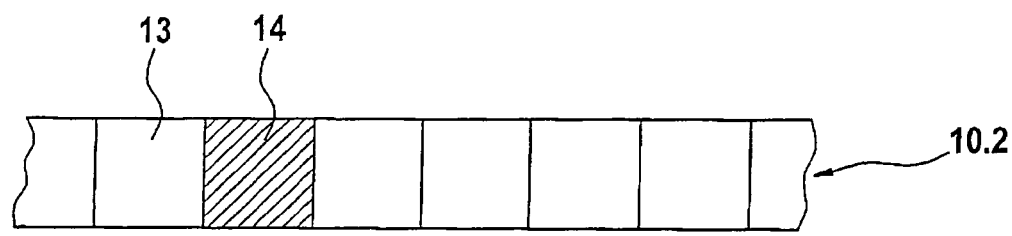
Figure 10C:
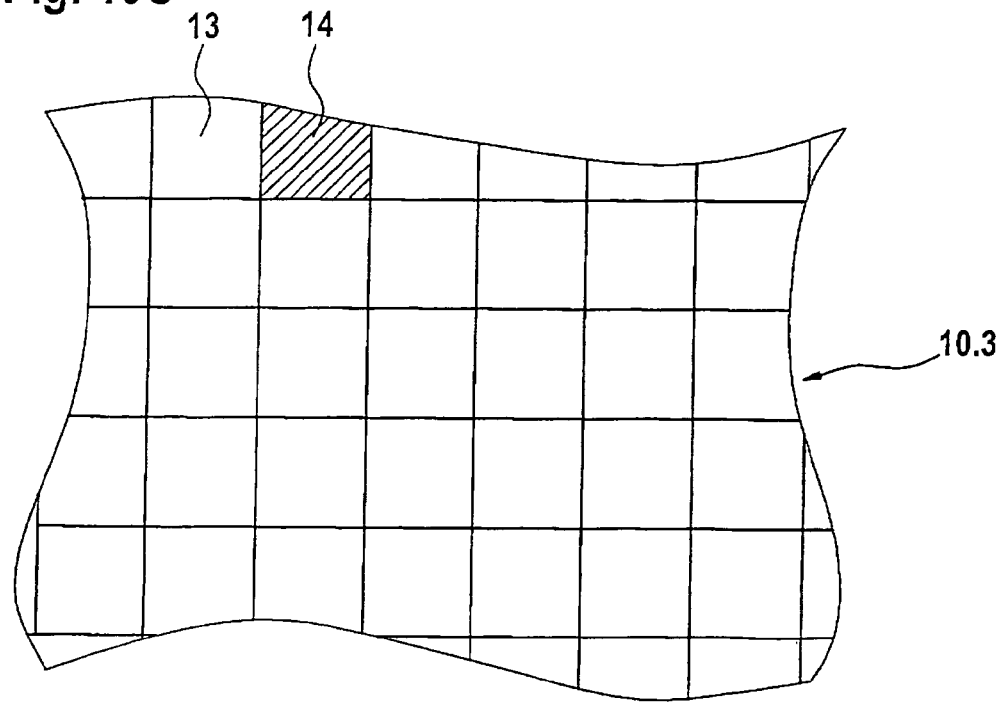

FIGS. 10A to 10C show different possible geometries of image detectors. The image detectors can each be designed using different technologies, thus for example, as CCD or CMOS sensors.

The image detector 10.1 shown in FIG. 10A shows the simplest possible case of a point sensor having two sensor elements 13, 14.

In FIG. 10B, a section of an image detector 10.2 consisting of a line comprising point sensors 13, 14 is illustrated.

FIG. 10C shows a laminar image detector 10.3 necessary for 3D imaging in a single exposure. Here, the sensor elements 13, 14 can be configured in various ways.

As in the case of a laminar image detector 10.3 illustrated in FIG. 10C, FIGS. 11A to 11C show different possibilities of configuring the sensor elements 13, 14. The design of the moveable aperture 12 must be adapted to the arrangement of the pairs of sensor elements.

Figure 11A:
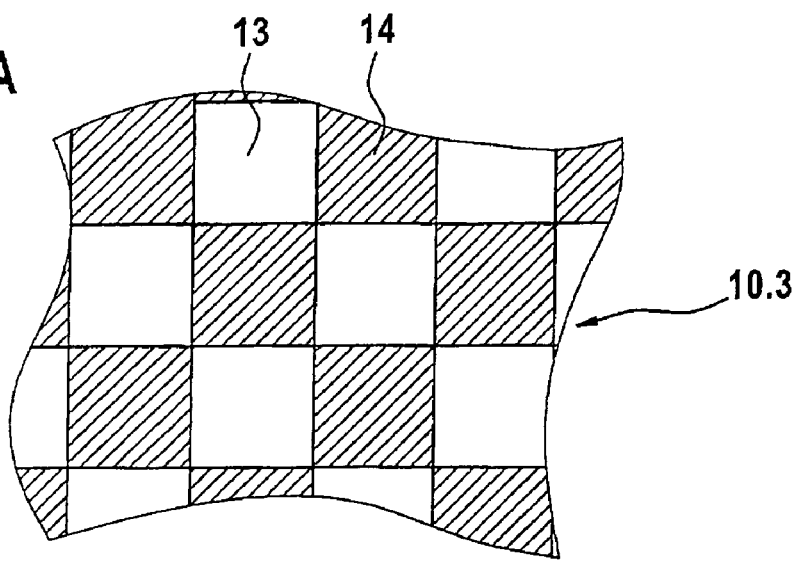
FIGS. 11A to 11C show different possibilities of configuring the sensor groups.

In FIG. 11A the groups of sensor elements are distributed in a checkered manner over the surface. The translucent areas of the moveable aperture must in this case likewise be designed in a checkered manner.

Figure 11B:
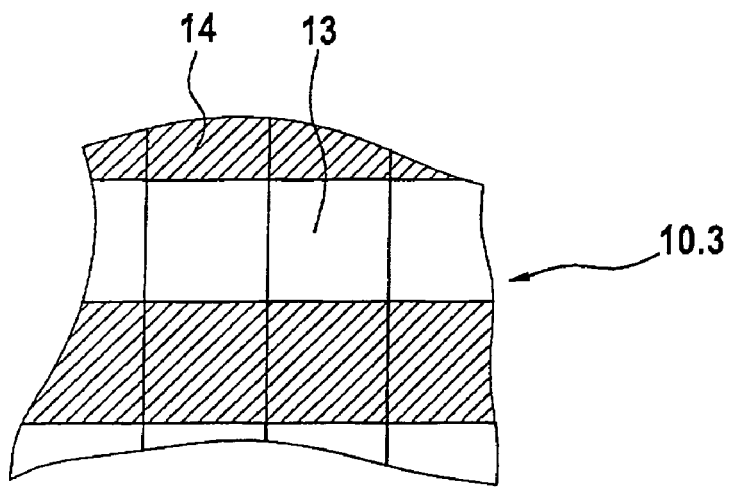

FIG. 11B shows a linear arrangement of corresponding groups of sensor elements, in which the interacting sensors 13, 14 are arranged one below the other.

Figure 11C:
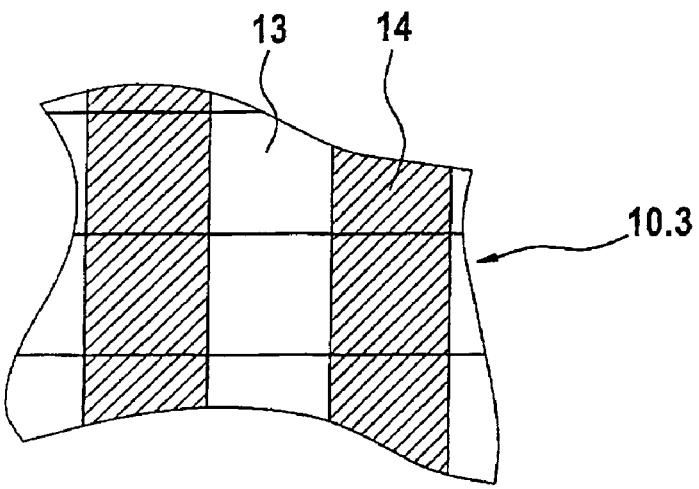

FIG. 11C differs from FIG. 11B only in showing a column arrangement instead of a linear arrangement of the groups of sensor elements. Here as also in FIG. 11B, the aperture is an appropriately aligned striped aperture.

Figure 12A:
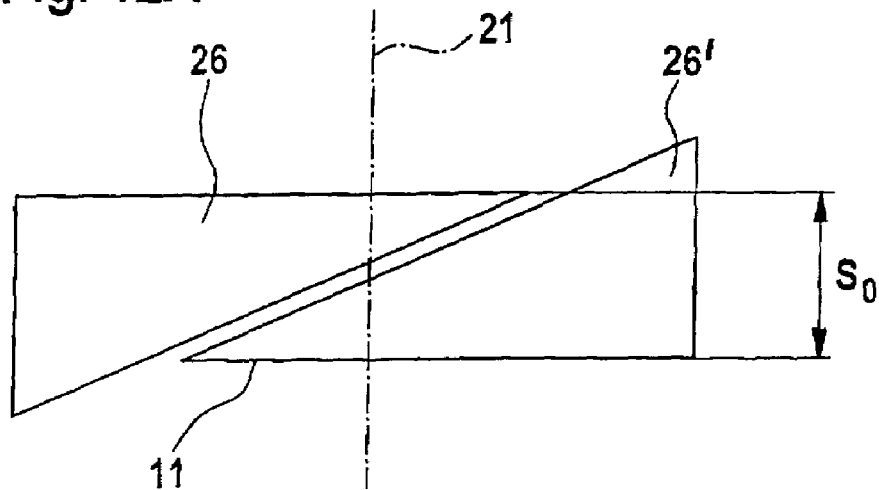
FIGS. 12A and 12B show an arrangement of glass wedges which can be used according to an improved development of the invention for changing the optical thickness of the beam path, in two positions.
Figure 12B:
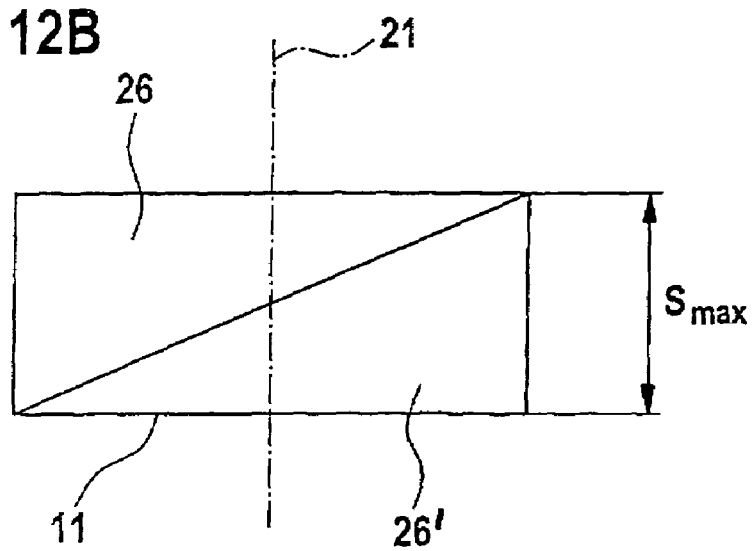

In FIGS. 12A to 12B, an embodiment of the means for adjusting the length of the optical path 11 is proposed. Two glass wedges 26 and 26' are arranged in the beam axis 21 such that they can be displaced relatively to one another. The effective thickness S can be changed by a corresponding displacement of the wedge. The change of the length of the optical path d between the aperture array 3 and the image plane is achieved within the effective thickness S by the change in the aperture angle of the light cone caused by refraction of the light at the surface so that lengthening or shortening of the focal length of the imaging optics 4 is achieved depending on the optical density of the wedge.

FIG. 12A shows the wedge 26, 26' with a small effective thickness $S_0$, as is present at time $t_0$.

By contrast, FIG. 12B shows a position of the two glass wedges 26 and 26' in which the latter provide a maximum thickness $S_{max}$.

The image detector 10 has an exposure time T for an image consisting of n×m pixels. The image detector 10 is designed in such a way that at least two sensor elements 13, 14 are assigned to each point of the aperture array 3 by the receiver optics 9 and additional elements, if appropriate. Regarded logically, the image detector 10 thus comprises two n/2×m matrices of sensor elements using an exposure time T for obtaining image information. The image detector 10 further comprises means which permit the sensitivity of one sensor element matrix to decrease continuously during time T, eg from a maximum value to zero and the sensitivity of the other sensor element matrix to increase, eg from zero to a maximum value.

The structure of the image detector 10 according to FIG. 8 consists of a beam splitter 24 and two electronic image sensors 10, 10', which can be in the form of, say, CCD or CMOS sensors. The pixel matrices of both the image sensors 10, 10' form the previously described two n/2×m pixel matrices on which the same image is reproduced. Both the sensors 10, 10' contain means 25, 25' for varying the sensitivity, eg LCD plates, which are located in the observation beam path 7 between the beam splitter 8 and the image sensor 10. Alternatively to the LCD plates, the sensitivity can be changed directly by electronic means acting on the image sensors, provided this is permitted by the sensor technology used.

In the typical use of laminar altitude measurement of objects with sensor element configurations as described with reference to FIG. 11B and FIG. 11C, in the case of typical values of n=500, m=500, the aperture 12 is in the form of a striped pattern. Alternatively to a mechanically moving aperture, an LCD striped pattern can also be used in which adjoining stripes lie in front of interacting sensor elements and specifically change the sensitivity of the latter.

Figure 13:
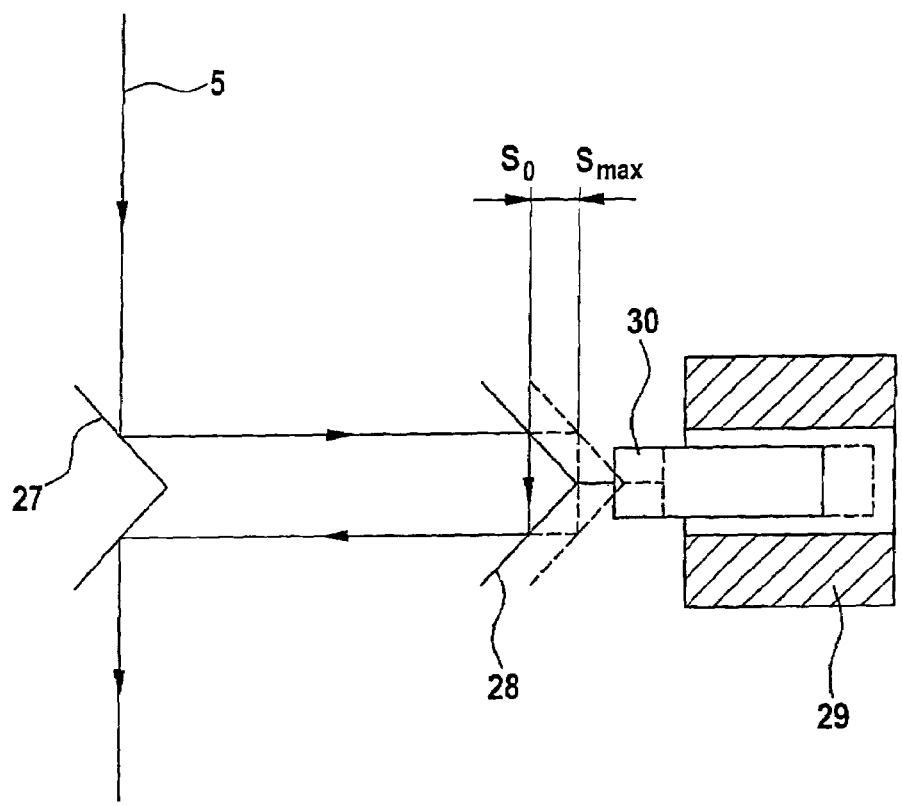
FIG. 13 shows an arrangement which can be used alternatively to that shown in FIG. 12 for changing the length of the optical path. Said arrangement is based on the use of reflectors, wherein one reflector is displaceable by means of moving coils. The reflector is shown in two different positions.

In FIG. 13, the change in the optical path is made possible by means of two reflectors 27 and 28, of which reflector 27 is fixed, according to the illustration, and the rear side of reflector 28 is fixed to a magnet 30 pertaining to a moving coil 29. These moving coils are known from the prior art, for example from the construction of loudspeakers, and therefore require no further explanation. Two positions of reflector 28 and magnet 30 are illustrated, the position illustrated by dashed lines corresponding to a change in the length of the optical path equal to $2 \times S_{max}$ in relation to the position illustrated by continuous lines.

Advantageously the scanning device is such that the image detectors 10 are flat panel sensors and the altitude measurement of the object is carried out in the exposure period T of the image detector. However, it is also possible to work with line sensors instead of flat panel sensors and to scan an object line-by-line. Theoretically, it is possible to divide the scan into a plurality of successive exposure periods instead of traveling through the entire altitude measurement region during a single exposure period T.

LIST OF REFERENCE NUMERALS

1 light source
2 imaging optics
3 aperture array
4 imaging optics
5 light beam
6 object
6' object point
6.1 cavity
7 observation beam path
8 deflecting means
9 receiver optics
9' imaging optics
10 image detector
10' image detector
10.1 image detector, in the form of a point sensor
10.2 image detector, in the form of a line sensor
10.3 image detector, in the form of a flat panel sensor
11 means for changing the length of the optical path
12 moveable aperture
13 sensor element
14 sensor element
15 dark aperture area
16 bright aperture area
17 movement direction of the aperture
21 axis
22 focal point; 22', 22" in different positions
23 light spot
24 beam splitter
25 means having variable translucence
25' means having variable translucence
26 glass wedge
26' glass wedge
27 reflector
28 displaceable reflector with magnet
29 moving coil

The invention claimed is:

1. A scanning system for an object comprising:
a light source for emitting illuminating light along an illuminating light path,
an aperture array positioned between the light source and the object,
imaging optics positioned between the aperture array and the object for focusing the illuminating light onto the object,
means positioned between the aperture array and the object for changing a length of an optical path between the aperture array and the object,
an image detector for detecting backscattered light from a point on the object that passes back through said imaging optics along an observed beam path, said image detector comprising two sensor elements for detecting backscattered light from the object point, and
means for adjusting an accumulation of charges in the two sensor elements from intensity of light in the observed beam path during an exposure period (T) so that a correlation with the length of the optical path of an image plane from the imaging optics is created to enable reconstruction of an altitude coordinate (zs) of the object from a distribution of levels of intensity acquired from the two sensor elements during the exposure period (T), said means altering sensitivity of said two sensor elements and/or translucence in the observed beam path between said imaging optics and said image detector.

2. The scanning system as defined in claim 1, wherein said aperture array enables a plurality of object points to be detected, and said image detector includes as many groups of sensor elements as there are object points to be detected.

3. The scanning system as defined in claim 2, including deflecting means in said observed beam path between said object and said image detector for deflecting said observed beam path.

4. The scanning system as defined in claim 3, wherein said deflecting means is a beam splitter.

5. The scanning system as defined in claim 3, wherein said deflecting means is positioned between said imaging optics and said light source.

6. The scanning system as defined in claim 3, wherein said deflecting means is positioned between said aperture array and said light source.

7. The scanning system as defined in claim 1, including a moveable aperture which at least partially shades said sensor elements depending on amount of movement of said aperture.

8. The scanning system as defined in claim 7, wherein movement of said aperture causes a reduction of shading of the at least one sensor element and an increase in shading of said at least one other sensor element.

9. The scanning system as defined in claim 7, wherein said aperture shades, in an initial position, a part of said sensor elements completely and, in an end position, another part of said sensor elements completely and, in an intermediate position, shades both a part of certain sensor elements and a part of the other certain sensor elements.

10. The scanning system as defined in claim 9, wherein a degree of shading of said part of said sensor element is complementary to a degree of non-shading of the other part of said sensor element.

11. The scanning system as defined in claim 1, wherein said means consists of an electronically controlled optical element of variable translucence.

12. The scanning system as defined in claim 11, wherein said aperture array is designed for two-dimensional scanning of said object.

13. The scanning system as defined in claim 12, including regulating means for adjusting a position of said aperture array such that regions not imaged in a first scan due to pulse duty ratio of said aperture array are imaged in a second scan.

14. The scanning system as defined in claim 2, wherein an average scanning distance of said aperture array is in accord with a desired measuring accuracy.

* * * * *